United States Patent [19]

Doherty

[11] Patent Number: 5,668,306

[45] Date of Patent: Sep. 16, 1997

[54] SOIL ANALYSIS METHOD INCLUDING SEPARATE ANALYSES OF CORE SAMPLE STRATA

[76] Inventor: David L. Doherty, 3301 W. 91st St., Leawood, Kans. 66206

[21] Appl. No.: 649,792

[22] Filed: May 17, 1996

Related U.S. Application Data

[62] Division of Ser. No. 430,338, Apr. 28, 1995, abandoned.

[51] Int. Cl.$^6$ .......................... G01N 15/08; G01N 15/10; G01N 33/24
[52] U.S. Cl. ................................................................ 73/38
[58] Field of Search ...................................................... 73/38

[56] References Cited

U.S. PATENT DOCUMENTS 5,372,037  12/1994  Butt .................................. 73/863.52 X

OTHER PUBLICATIONS

Soiltest Incorporated, 1960–1962, Edition II, pp. 62–63.
Copper et al., *The Mechanics of Engineering Soils*, McGraw-Hill Book Company, Inc. 1949, pp. 30–46.
Hammond, *Foundations and Soil Properties*, Macdonald and Co., 1961, pp. 22–29.
Knight, *Soil Mechanics for Civil Engineers*, Edward Arnold and Co., 1948, pp. 96–105 and 126–127.
Plummer et al., *Soil Mechanics and Foundations*, Pitman Publishing Corporation, 1940, pp. 44–58.

*Primary Examiner*—Michael Brock
*Assistant Examiner*—Daniel S. Larkin
*Attorney, Agent, or Firm*—Hovey, Williams Timmons & Collins

[57] ABSTRACT

An improved soil analysis is provided which provides accurate data representative of actual physical conditions of the soil. Preferably, the method involves first obtaining a core sample of soil having an essentially undisturbed naturally occurring compaction and stratification and subjecting at least a portion of this undisturbed core sample to one or more physical tests such as water permeability, water holding capacity and porosity tests. Thereafter, the sample portion is divided into vertically aligned strata and the latter are individually tested for organic content, silt and clay content and sand content.

6 Claims, 5 Drawing Sheets

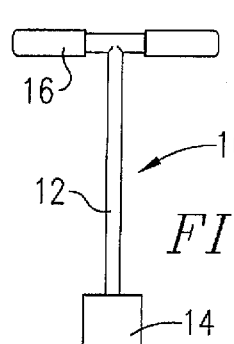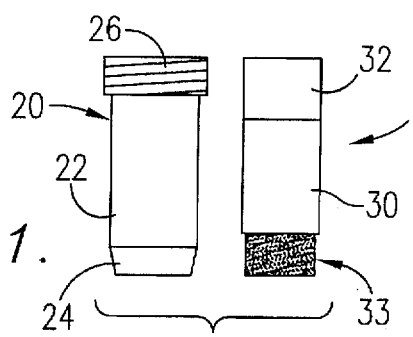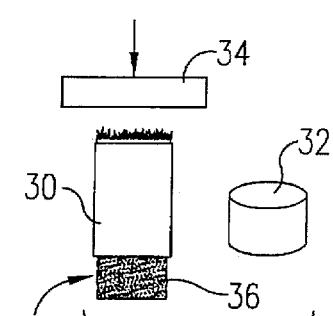
FIG.1.  FIG.2.  FIG.3.
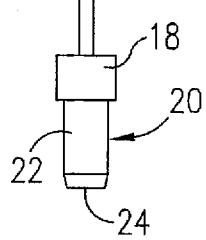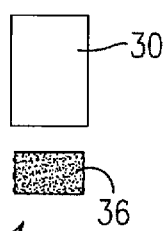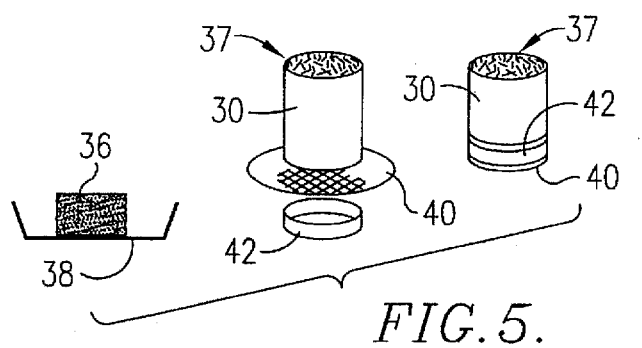
FIG.4.  FIG.5.
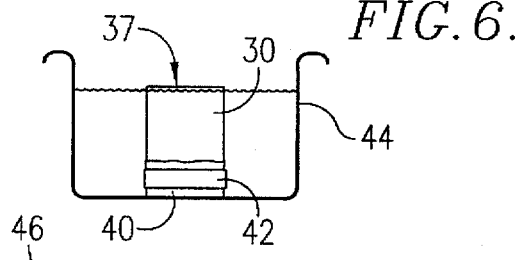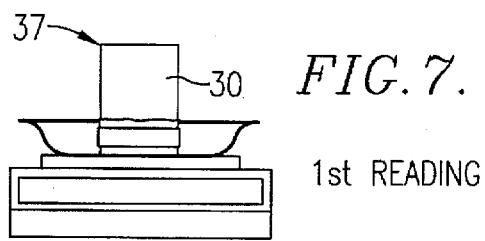
FIG.6.  FIG.7. 1st READING
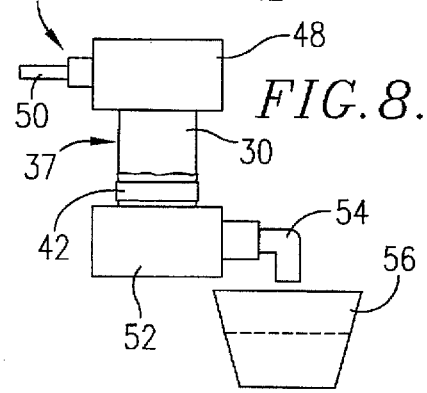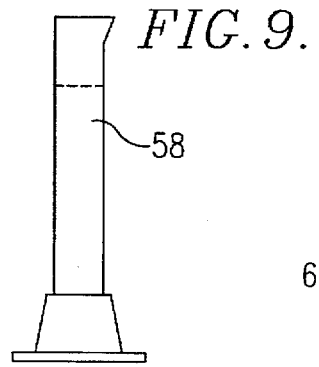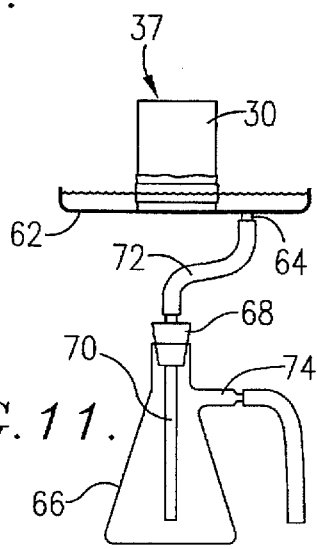
FIG.8.  FIG.9.
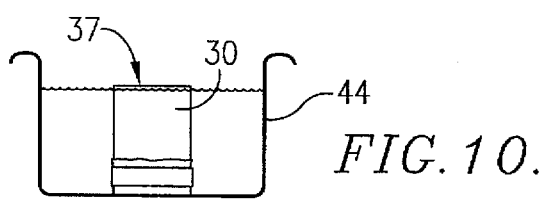
FIG.10.  FIG.11.

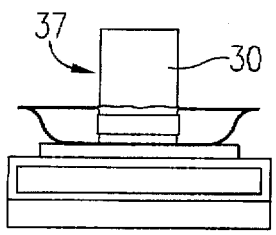
2nd READING
*FIG. 12.*
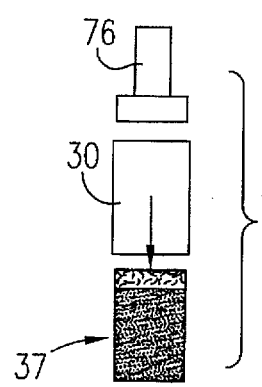
*FIG. 13.*
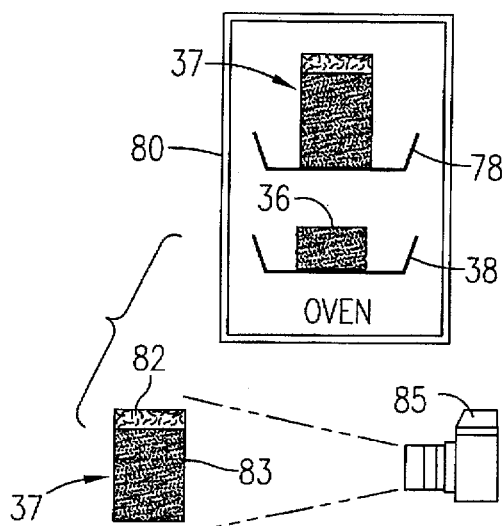
*FIG. 14.*
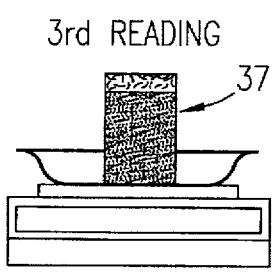
3rd READING
*FIG. 15.*
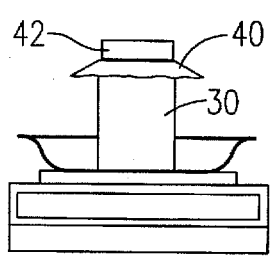
*FIG. 16.*
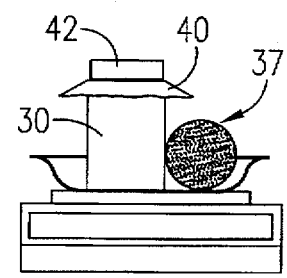
*FIG. 17.*
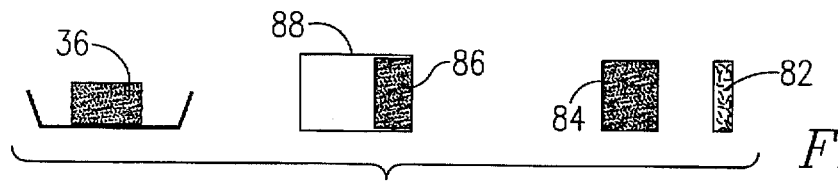
*FIG. 18.*
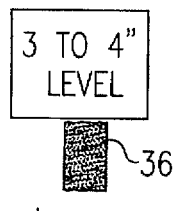
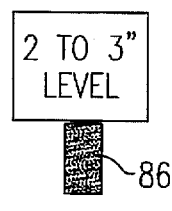
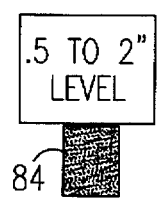
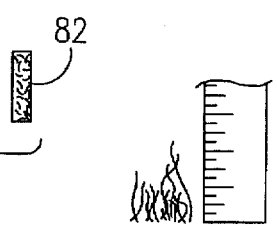
*FIG. 19.*
*FIG. 21.*
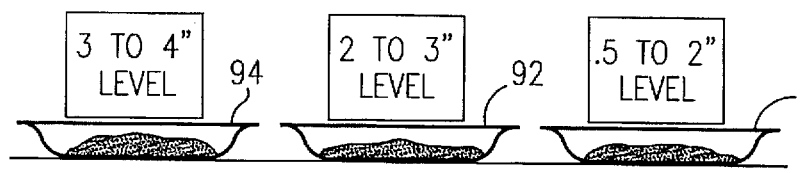
*FIG. 20.*

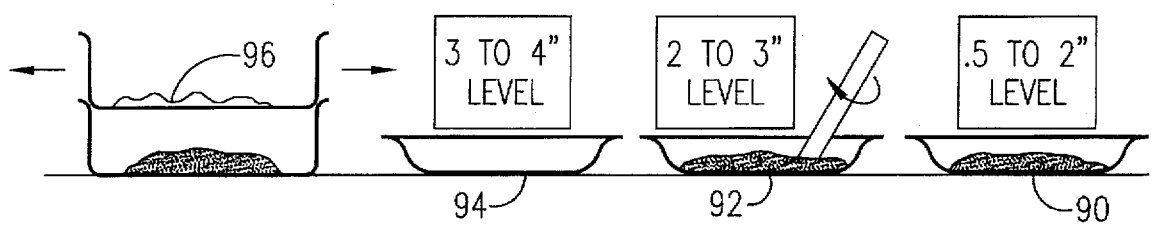
FIG.22.
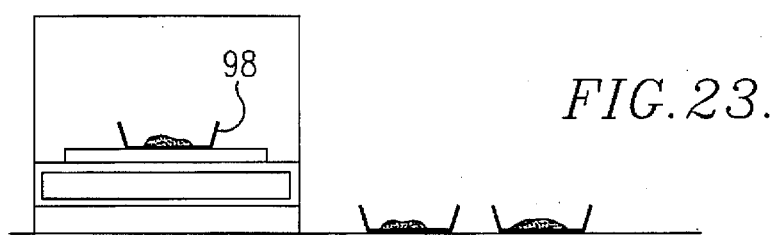
FIG.23.
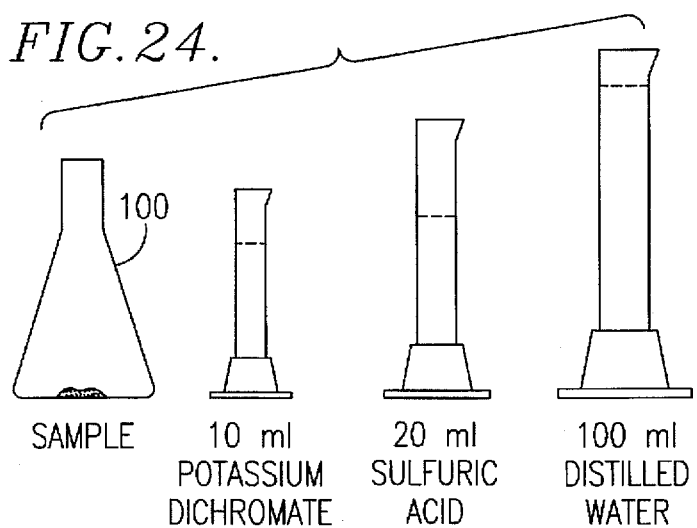
FIG.24.
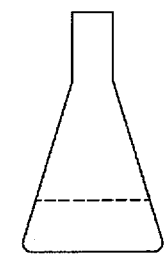
FIG.25.
CALIBRATION STANDARD
10 ml POTASSIUM DICHROMATE
20 ml SULFURIC ACID
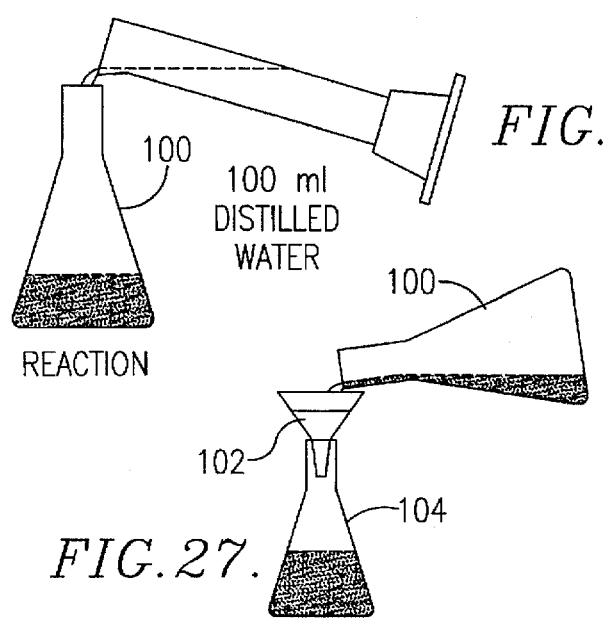
FIG.26.
FIG.27.
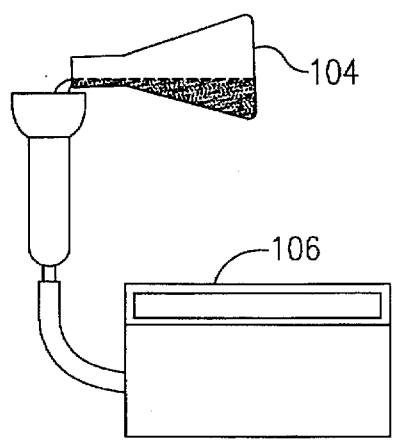
FIG.28.

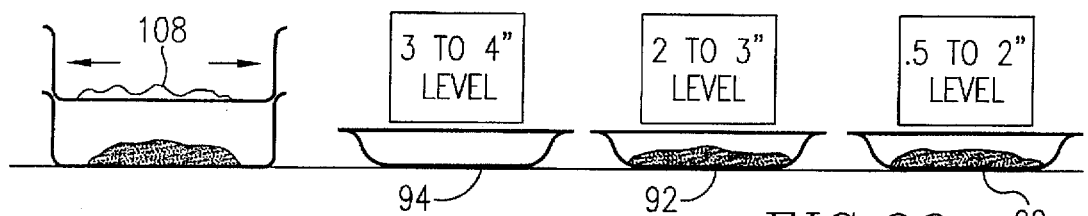
FIG.29.
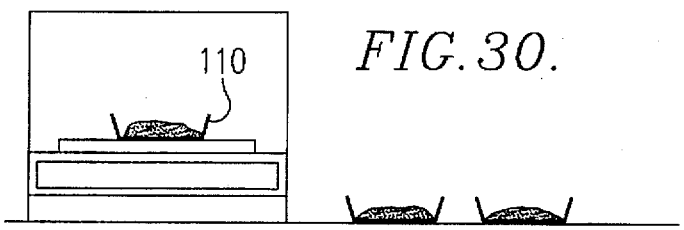
FIG.30.
FIG.31.
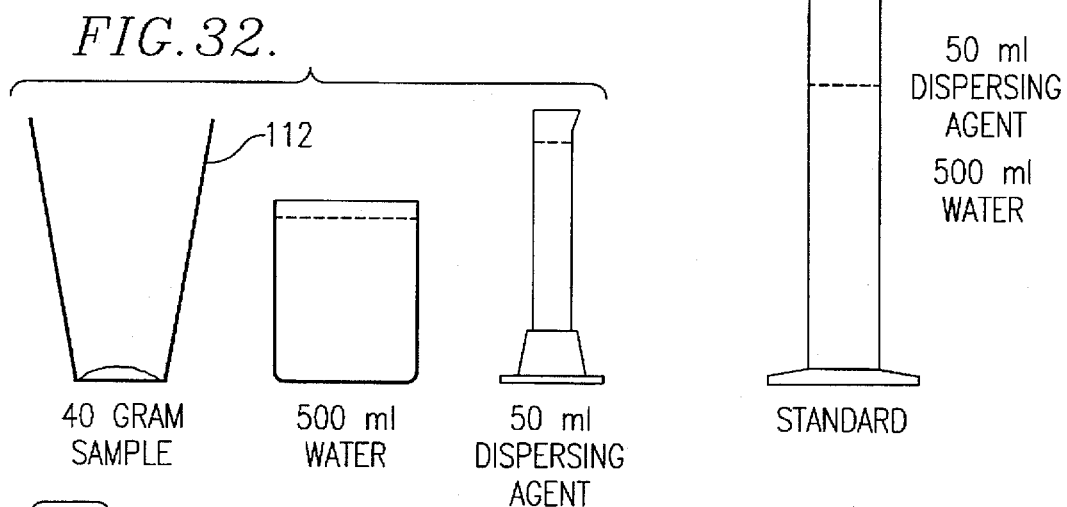
FIG.32.
FIG.33.
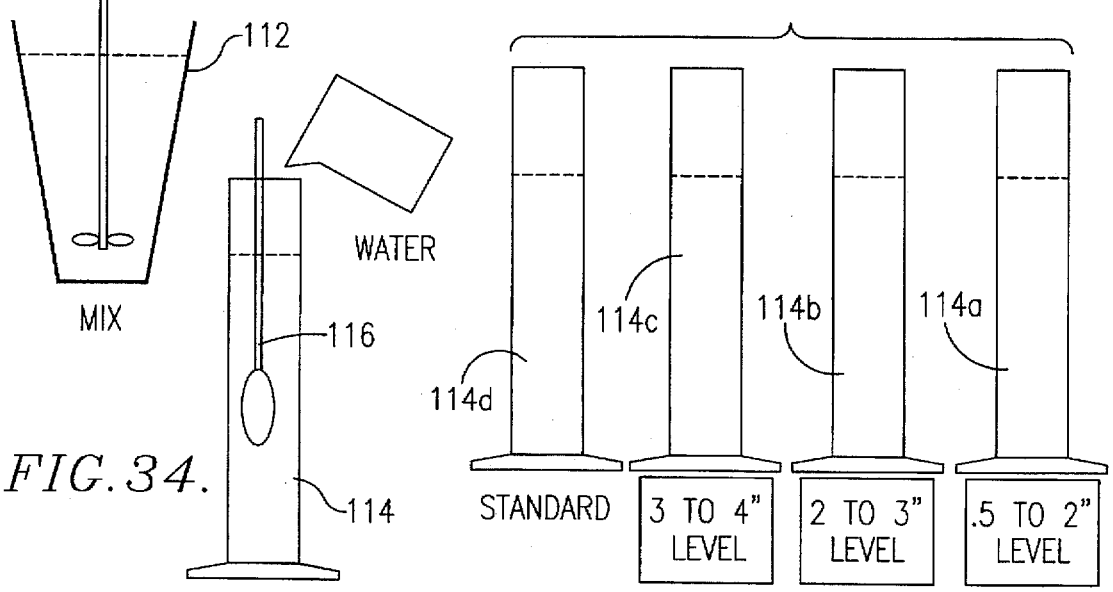
FIG.34.
FIG.35.

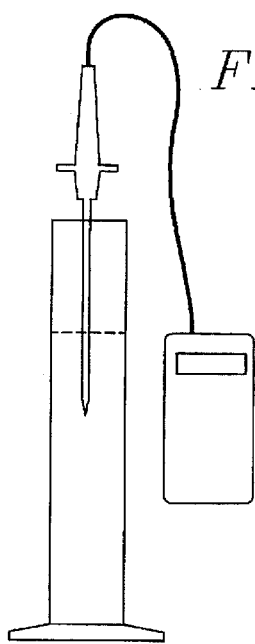
FIG.36.
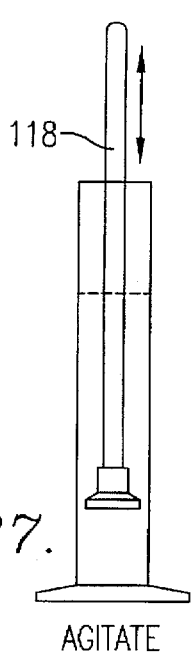
FIG.37.
AGITATE
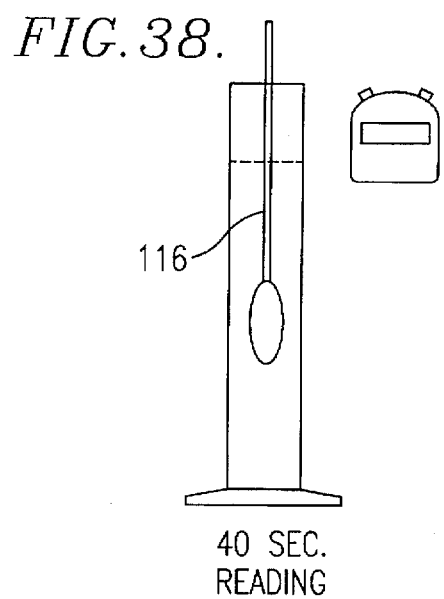
FIG.38.
40 SEC. READING
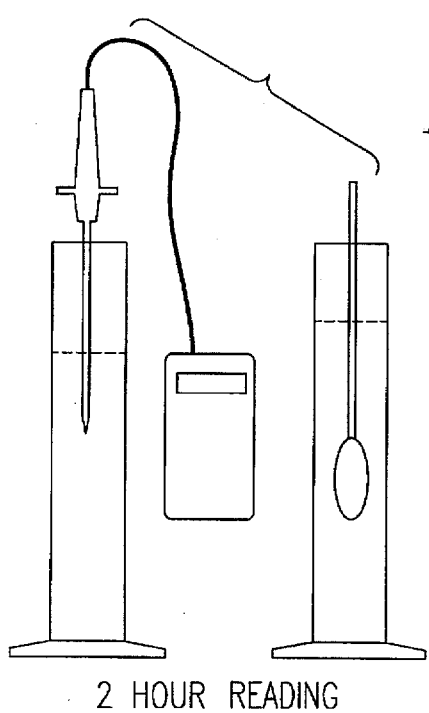
2 HOUR READING
FIG.39.
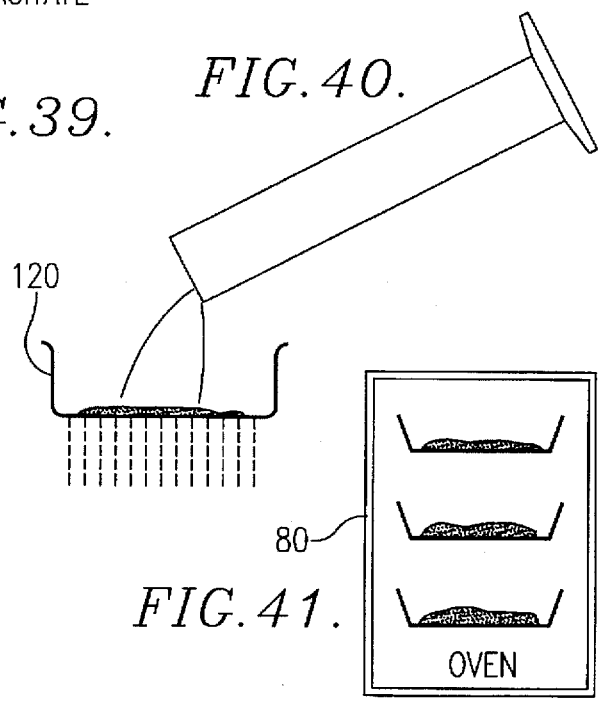
FIG.40.
FIG.41.
OVEN
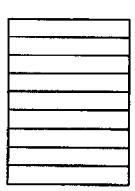
FIG.42.
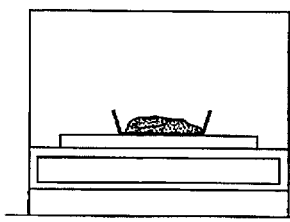
FIG.43.

SOIL ANALYSIS METHOD INCLUDING SEPARATE ANALYSES OF CORE SAMPLE STRATA

This application is a divisional of application Ser. No. 08/430,338, filed Apr. 28, 1995, now abandoned.

BACKGROUND OF THE INVENTION

1. Field of the Invention

The present invention is broadly concerned with an improved method for analyzing soil samples in order to ascertain the physical properties thereof. More particularly, the invention pertains to such a method wherein, in one aspect, a soil sample having essentially undisturbed, naturally occurring compaction and stratification properties is analyzed for water infiltration rate, water holding capacity and porosity; the sample is then divided into a plurality of strata which are individually analyzed for sand, silt, clay and organic content. The method of the invention yields data which can accurately pinpoint problem areas in the soil which would not be determinable by conventional techniques.

2. Description of the Prior Art

Soil testing techniques have long been employed for the analysis of turf and seed beds. For example, golf course green's keepers routinely send seed bed samples to laboratories in an effort to determine the condition of the seed bed. It is believed that such tests aid the green's keeper in determining the proper course for maintenance of the seed bed, e.g., the need for soil aeration, watering schedules and/or chemical applications.

Conventional soil testing techniques used for these purposes have involved the step of first "plugging" the soil to obtain a vertical soil sample of perhaps 4 inches in height. Such a sample plug is then sent to the lab for analysis. The first laboratory step involves pulverizing the plug below the thatch layer with mixing to create a homogenized soil sample. This homogenized soil is then compacted by the laboratory into a laboratory plug which is analyzed by known techniques for water filtration rate, water holding capacity, and porosity. In addition, the homogenized, laboratory compacted plug is analyzed for textural properties including sand, silt and clay contents.

A persistent problem in the art is that such conventional soil plug tests do not yield realistic results which can be used to develop a seed bed maintenance program. That is, a conventional battery of tests may lead to the conclusion that the seed bed is in perfectly acceptable condition; yet, the green's keeper knows from experience that the seed bed has problems, usually resulting in sparse grass cover and lackluster growth in hot, dry weather. When soil tests seemingly indicate that the seed bed is within acceptable limits, the green's keeper often concludes that the problem is of a chemical rather than of a physical nature. This may lead the green's keeper to overapply fertilizers or herbicides, which can in fact actually exacerbate the real problem.

Soil compaction is recognized as one of the major problems to be overcome in producing good turf. This is particularly true on golf courses where player traffic and maintenance equipment subjects the soil to constant packing. The fact that golfers demand that grasses be kept moist enough to hold a golf shot serves to intensify the compaction problem. However, as explained above, conventional soil testing methods do not and cannot actually measure in any meaningful way the real compaction of soil samples. This stems from the fact that conventional testing requires that a given field sample be first pulverized, mixed and laboratory compacted. As a consequence, the actual conditions of the soil are often not reported by the known testing techniques.

There is accordingly a real and unsatisfied need in the art for an improved soil testing method which gives results which more closely approximates actual, real world seed bed conditions.

SUMMARY OF THE INVENTION

The present invention overcomes the problems outlined above, and provides an improved soil testing method which is conducted in two stages. In the first stage, a core sample of soil is obtained having essentially undisturbed, naturally occurring compaction and stratification characteristics. At least a portion of this core sample is preserved in this naturally occurring condition and as such is subjected to a battery of tests. These tests include a water permeability test, a water holding capacity test, and porosity testing. In addition, as a part of a drying process, the essentially undisturbed sample is observed for the appearance of a dark layer of organic material. In preferred forms, such observation is obtained by repeatedly photographing the sample as it dries.

After this initial battery of tests is completed, the core sample portion is divided into a plurality of vertically aligned strata, and each of these strata is analyzed for organic content, silt and clay content, and sand content. Preferably, the latter test includes determining the particle size distribution of the sand content in each of the strata.

BRIEF DESCRIPTION OF THE DRAWINGS

FIG. 1 is a schematic view of the plunger apparatus employed to obtain an initial soil plug sample for testing in accordance with the present invention;

FIG. 2 is a schematic view illustrating the endmost outer cutter tube of the FIG. 1 apparatus, along with the inner two-part tubular assembly disposed within the cutter tube, showing a plug of soil extending from the bottom of the tubular assembly;

FIG. 3 is a schematic representation of the step of shifting the sample plug downwardly within the primary tubular body of the tubular assembly;

FIG. 4 is a schematic view illustrating the step of first observing and measuring the feeder root length and density, and then severing the bottom portion of the sample plug below the tubular body;

FIG. 5 is a schematic representation of the next step of the preferred process wherein the severed bottom portion of the sample plug is placed in a holding pan, and the tubular body, containing the remainder of the sample plug, is equipped with a bottommost liquid-pervious retainer cloth;

FIG. 6 is a schematic view illustrating placement of the tubular body containing the remainder of the sample plug in a water bath for saturation of the remainder of the sample plug;

FIG. 7 illustrates the next step of the process wherein, after the sample plug remainder is saturated with water, the tubular body and saturated sample plug are weighed;

FIG. 8 illustrates the next step of the process wherein the tubular body and saturated sample plug remainder of FIG. 7 are placed in a permeameter for a five hour period;

FIG. 9 is a schematic representation of the next step wherein the volume of water collected from the permeameter is measured;

FIG. 10 is a view similar to that of FIG. 6 and illustrates placement of the tubular body and sample plug remainder in a second water saturation bath;

FIG. 11 is a representation of the next step of the process wherein the saturated sample plug remainder from FIG. 10 is placed on a tension table;

FIG. 12 is a view similar to that of FIG. 7 and illustrates the next step wherein the tubular body and sample plug remainder are weighed after the FIG. 11 tension table step;

FIG. 13 illustrates the step of removing the sample plug remainder from the primary tubular body;

FIG. 14 illustrates the next step wherein the sample plug remainder from FIG. 13 and the bottom portion of the sample plug are oven-dried, with periodic inspection of the sample plug remainder to visually ascertain and photograph the different soil appearances;

FIG. 15 is a schematic view illustrating a third weighing of the sample plug remainder after drying thereof;

FIG. 16 illustrates a tare weight step wherein the tubular body, cloth cover and retainer are weighed;

FIG. 17 illustrates a check weight step wherein the tare of FIG. 16 is weighed along with the dried sample plug remainder;

FIG. 18 illustrates the step of placement of the original bottom portion of the sample plug in a tray, and wherein the remainder of the sample plug is severed into three sections, namely a thatch section, a 0.5–2 inch level section and a 2 inch–3 inch level section;

FIG. 19 is a view illustrating all of the sections of the original sample plug;

FIG. 20 illustrates the next step in the process wherein all of the sample plug sections except the thatch section are pulverized and placed in respective pans;

FIG. 21 is the step of measuring the height of the root mass associated with the sample plug;

FIG. 22 illustrates the next step in the process wherein all of the pulverized sample plug sections are screened, and the pass-throughs from each plug section are thoroughly mixed;

FIG. 23 illustrates a step wherein one gram portions of each of the screened sample plug sections are put into separate pans;

FIG. 24 illustrates one of the screened test portions along with the reagents employed for ascertaining the organic content thereof;

FIG. 25 illustrates the step of preparing a liquid calibration standard containing potassium dichromate and sulfuric acid;

FIG. 26 illustrates the step wherein potassium dichromate and sulfuric acid have been added to each test portion in a separated flask and allowed to react for a ten minute period, whereupon distilled water is then added to terminate the reaction;

FIG. 27 illustrates the step of filtering the diluted reaction mixtures from the step of FIG. 26 into respective flasks;

FIG. 28 illustrates the step of spectrophotometrically analyzing each of the filtrates from the FIG. 27 step;

FIG. 29 illustrates the initiation of the Bouyoucous test wherein the remainder of the pulverized sample sections are individually screened through a #5 screen;

FIG. 30 depicts the step of weighing out 40 gram samples of each of the screened sections from the FIG. 29 step;

FIG. 31 illustrates the step of preparing a liquid standard for the Bouyoucous test containing dispersing agent and water;

FIG. 32 depicts the samples and reagents employed in the Bouyoucous test;

FIG. 33 illustrates the step of mixing each 40 gram screened sample section with 500 milliliters of water and 50 ml of dispersing agent, with mixing;

FIG. 34 illustrates the step of placing each mixture from the FIG. 33 step in a graduated cylinder along with a hydrometer, and adding water thereto to a liter level;

FIG. 35 illustrates the four cylinders resulting from steps 31–34, i.e., a standard, and respective cylinders containing the test portions of the three plug sections;

FIG. 36 depicts the step of measuring the temperature of the liquid within each cylinder of FIG. 35 after the latter are allowed to stand overnight;

FIG. 37 illustrates the step of agitating the liquid content of each of the cylinders illustrated in FIG. 35;

FIG. 38 illustrates the next step wherein the suspended silt and clay content of each of the cylinders of FIG. 35 is measured using a hydrometer;

FIG. 39 depicts a second temperature and suspended clay reading taken on each test cylinder, after two hours;

FIG. 40 illustrates the step of pouring the contents of each test cylinder onto a #270 screen to separate the silt and clay content thereof from the sand content;

FIG. 41 depicts the step of drying the recovered sand content of each of the test cylinders from the FIG. 41 step;

FIG. 42 illustrates the step of screening each dried sand sample through a series of size classification screens; and FIG. 43 illustrates the step of weighing the collected sand amounts on each of the screens illustrated in FIG. 42.

DETAILED DESCRIPTION OF THE PREFERRED EMBODIMENTS

Turning now to the drawings, the preferred turf analysis method will now be described. Broadly speaking, this method involves initially providing a plug of the turf to be tested which is approximately four inches in depth. Thereafter, a bottom portion of this plug (nominally about 1 inch in height) is separated and the remainder of the plug is saturated and subjected to a permeameter and tension table test. This plug remainder is then dried and observed over time to ascertain the vertical level of organic and other water holding material therein; the plug remainder is then severed into two additional sections. All three of the plug sections are then pulverized and respective samples of each such pulverized section are tested for organic content, suspended solids (silt and clay) and sand; the latter is then size classified.

In more detail, the initial turf plug is preferably obtained through using a conventional plugger 10 illustrated in FIG. 1. The plugger 10 includes an upright shaft 12 equipped with a sliding weight 14 and an uppermost handle 16. The lower end of the shaft 12 includes an anvil 18 and a metallic tubular cutter assembly 20. The cutter assembly 20 includes an outermost tubular section 22 terminating in a beveled, lowermost cutting edge 24; the upper end of the section 22 is threaded as at 26 into anvil portion 18. The overall cutter assembly 20 also includes an internal tubular assembly 28 made up of a lower main tube 30 and an upper tubular extension 32; in practice, the tube 30 and extension 32 are taped together. The assembly 28 fits within outermost tubular section 22 and is retained therein by means of a lower internal ledge (not shown).

In use, the plugger 10 is positioned directly above a turf area to be plugged, and the edge 24 is placed at turf level.

Thereafter, the weight 14 is raised and dropped onto anvil 48 in order to drive the cutter assembly 20 into the turf until the lower surface of anvil 18 is reached. The plugger 10 is then removed serving to pull from the turf a cylindrical plug 33 of approximately 4 inches in height.

In the next step (FIG. 2), the tubular assembly 22 is detached from section 18, and assembly 22 is removed from section 18, and extension 32 is detached from tube 30. At this point, a block 34 is used to push the upper surface of plug 33 downwardly until the thatch region thereof is adjacent the upper edge of tube 30, thus presenting a lowermost plug section 36 (FIG. 3). The latter is then severed from the remainder 37 of the plug 33 within the confines of tube 30 (FIG. 4). This plug section 36 is then placed within a holding tray 38 (FIG. 5). The remainder 37 preferably has a height of at least 2 inches (FIG. 5).

The lower surface of the remainder of the plug 33 within tube 30 is then covered with a liquid-pervious cloth 40, and the latter is held in place by a resilient band 42 (FIG. 5). This assembly is then immersed in an ambient temperature water bath 44 (FIG. 6) and the plug section remainder 37 is soaked until saturated. After saturation is achieved, the assembly containing the sample plug remainder 37 is weighed to give the "first reading (FIG. 7)."

After weighing, the assembly is subjected to a permeation test (see FIG. 8). In this regard, a permeameter 46 is employed which includes an uppermost header 48 attached to a water supply via conduit 50. The permeameter 46 also includes a base 52 having a water outlet 54. In use, the assembly including tube 30 and plug remainder 37 is placed within the permeameter and a predetermined water head (normally ¼ inch in height) is maintained across the upper surface of the plug remainder 37 for five hours. This causes water to permeate through the plug remainder 37, and such water is ultimately collected in cup 56. The volume of water within the cup 56 at the end of the permeation test period is then measured by any convenient means such as by using a graduated cylinder 58 (see FIG. 9).

After the permeation test, the plug remainder assembly is reimmersed in water bath 44 until saturation is again achieved (FIG. 10). Thereafter, the assembly is placed on a 40 cm tension table apparatus 60 to measure the water holding capacity of the portion 37 (FIG. 11). The apparatus 60 includes a shallow water tray 62 having a tubular gravitational outlet 64. A screen and two or three layers of chromatography paper or other media capable of preventing air entry at 40 cm tension are placed on the tray bottom (FIG. 11). A flask 66 is positioned below the tray 62 and is equipped with a stopper 68 and delivery tube 70 (FIG. 11). A conduit 72 interconnects outlet 64 and tube 70 as shown (FIG. 11). The flask 66 is also equipped with a lateral drain port 74 for drainage of water as the latter collects in the flask (FIG. 11). The vertical distance between the bottom of remainder 37 within tray 62 and the port 74 is 40 cm (FIG. 11) (see, Baver, L. D., Soil Physics, 3rd Ed., John Wiley & Sons, Inc. (1956). During the tension table test, water drainage is continued until equilibrium is reached, i.e., no further water drains from the plug remainder 37 FIG. 11.

The drained plug remainder assembly is then weighed on the scale illustrated in FIG. 12 to obtain a "second reading." Thereafter, the plug remainder 37 is removed from tube 30 through the use of a manual plunger 76 or the like (FIG. 13). The plug remainder 37 is then placed within a tray 78, and this is placed within a drying oven 80. At the same time, the original lowermost plug section 36 in tray 38 is also dried. The oven 80 is normally set a temperature of from about 105°–130° C. and is opened at regular intervals (typically every 5–10 minutes) in order that the plug remainder 37 can be observed. In this connection, during the drying process, a black layer representing the organic or other water holding material content of the plug 37 becomes visible. Over time, a fully defined layer or layers may be revealed which extend from the upper thatch layer 82 of the section 37 downwardly to a point midway between the ends of the section 37. An exemplary lower margin 83 for such a layer is illustrated in FIG. 14. During the drying process when the layering becomes fully visible, a camera 85 may be used to obtain time lapse photographs of this layering. In any case, after the layering is fully observed and photographed, the drying process is continued until the sections 36 and 37 are completely dry and the latter again assumes an essentially uniform appearance. Generally speaking, the complete drying cycle will take from about 3–8 hours, with 5 hours being very common.

After drying, the plug remainder 37 is again weighed to obtain the "third reading", or the "dry slice net weight (FIG. 15)." A tare weight is also obtained by weighing the tube 30, cloth 40 and retainer 42 (FIG. 16). Finally, a check weight (FIG. 17) is made using the tare of FIG. 16 along with the dried plug remainder 37.

In the next step, plug remainder 37 is subdivided to create a separate thatch layer 82, and two intermediate layers 84 and 86 (FIG. 18). For this purpose, an enlarged severance tube 88 is used, allowing a clean cut between the respective sections. As best seen in FIG. 19, this procedure yields, with the original lowermost plug section 36, a total of four plug sections from the original turf plug 33. These are generally referred to as the thatch plug 82, the "0.5–2 inch level plug" (section 84, the "2 inch–3 inch level plug" (section 86), and the "3 inch–4 inch level plug" (section 36).

These level plugs 84, 86 and 36 are then individually pulverized and placed in respective pans 90, 92, 94 (FIG. 20). Also, the root mass from the thatch layer 82 is measured (FIG. 21). The three level plugs described above are then subjected to an organics content test. In the first step (FIG. 22), the contents of pans 90–94 are individually screened through an 18-mesh screen 96, and nominal 1 gram samples (usually about 1.01–1.015 g) of each of the screened materials are collected on individual trays 98 (FIG. 23). A series of reagents are employed for the organics test as illustrated in FIG. 24. In particular, each organic test for each 1 gram sample requires 10 milliliters of potassium dichromate (100%), 20 milliliters of concentrated sulfuric acid (90%), and 100 milliliters of distilled water. A calibration standard is also prepared for these tests which includes a combination of 10 milliliters of the potassium dichromate and 20 milliliters of the sulfuric acid (FIG. 25). In the first step of each test (FIG. 27), the pulverized sample of material is placed within a flask 100, and the previously prepared potassium dichromate and sulfuric acid are added thereto. This initiates a chemical reaction within the flask 100 which is allowed to proceed for 10 minutes (FIG. 26). At the end of the 10 minute reaction (FIG. 28) period, the distilled water is added to the flask 100 which terminates the reaction. As illustrated in FIG. 27, each reaction mixture is then passed through a filter 102 into a second collection flask 104. This filtrate is then spectrophotometrically analyzed using a conventional spectrophotometer 106 (e.g., a Hach DR-2000). The spectrophotometric measurements are taken at a wavelength of 610 nm and the results recorded. A similar measurement is taken of the aforementioned calibration standard.

In the next stage of the analysis, a Bouyoucous test is performed on each of the pulverized samples within pans 90, 92, 94. In particular, the entire contents of each of these pans are first screened through a #5 screen 108 (See FIG. 29) and nominal 40 gram samples of each of these screened materials are collected on trays 110. In order to complete the Bouyoucous test, each 40 gram sample is placed within an upright container 112, and 500 milliliters of water is added thereto. In addition, 50 milliliters of dispersing agent is incorporated into the mixture. This dispersing agent is preferably a conventional cleanser, e.g., granular Calgon cleanser. Using this granular material, the dispersing agent is made by dissolving 100 grams of the Calgon in one liter of water. A standard is also prepared which contains 500 milliliters of water and 50 milliliters of the same dispersing agent. In the next step, the mixtures within the containers 112 are vigorously mixed for 5–7 minutes using a mechanical stirrer or shaker (FIG. 33).

Referring to FIGS. 34–35, the next step for each of the mixed samples involves placement in an upright graduated cylinder 114 along with a conventional hydrometer 116. Water is added to the cylinder 114 to a level of 1 liter. This is also done for the described standard, thus creating four cylinders 114a–114d respectively containing the material from the plug sections 84, 86 and 36 with the defined quantity of liquid, and the liquid standard.

The cylinders 114a–114d are allowed to stand overnight to achieve temperature stabilization, and then the temperature of the contents of each cylinder is taken (FIG. 36). The liquid contents are then agitated using a manual plunger 118 to create a substantially homogeneous dispersion (FIG. 37). The hydrometer 116 is then used and a measurement after a period of 40 seconds for each cylinder is recorded to obtain a measurement of suspended solids (silt and clay) for each cylinder (FIG. 38). Each of the cylinders are then allowed to set for an additional 2 hours, whereupon the temperature of each cylinder's content is taken and an additional hydrometer reading is taken (FIG. 39). The latter measurement gives an indication of the suspended clay content of each cylinder 114a–114c. It will of course be understood that these same measurements are made with the liquid-only standard cylinder 114d.

The contents of each cylinder 114a–114c are then passed through a #270 screen 120, thus allowing the liquid, silt and clay to pass through the screen while retaining the sand content on the screen (FIG. 40). The collected sand for each cylinder is then washed with plain water. The sand collected from each of the test cylinders is then dried in oven 80 (105°–130° F. for a period of 5–8 hours) (FIG. 41). Thereafter, the dried sand from each test cylinder is size classified using an eight-screen classifier (#10, #18, #35, #60, #80, #100, #140 and #270 screens) (FIG. 42). In the final step, the amount of sand collected on each screen is individually weighed to give a maximum of 24 weight readings (FIG. 43).

It will thus be seen that the foregoing analysis generates the following data:

1. The "first reading" or "sat weight";
2. The amount of water collected from the permeameter;
3. The "second reading" or "40 cm weight";
4. The time lapse photographic record;
5. The "third reading" or "dry weight";
6. The tare weight;
7. The spectrophotometric readings for the three soil samples and the standard;
8. The 40 second temperature for each sample and the standard;
9. The 40 second hydrometer reading for each sample and the standard;
10. The 2 hour temperature for each sample and the standard;
11. The 2 hour hydrometer reading for each sample and the standard; and
12. The weight of each of the 24 size classifications of the dried sand.

This data is then employed to give the improved soil data of the invention. In particular, the first step involves calculation of the non-capillary porosity of the soil plug remainder 37. This is obtained by subtracting the 40 cm weight from the sat weight and dividing this by the total volume of the sample plug remainder 37 (this latter figure is simply calculated from the volume of the primary tubular body 30).

In the next step, the capillary porosity of the plug remainder 37 is calculated. This involves subtracting from the 40 cm weight, the total dry weight of the tare and sample remainder 37 (see FIG. 17) and dividing this result by the volume of the plug remainder 37.

The total porosity for the soil plug remainder 37 is then calculated as the sum of the non-capillary porosity and the capillary porosity. The solids content of the plug remainder 37 is calculated by subtracting the total porosity from 100.

In order to obtain the bulk density of the sample remainder 37, the third reading or dry weight is divided by the volume of the remainder 37. The emulated field water holding capacity is calculated by subtracting the total dry weight of the sample plug remainder 37 and tare (FIG. 17) from the 40 cm weight and dividing by the total dry weight of the sample plug remainder 37, and multiplying this result by 100 to give a percentage result.

The final datum for the physical evaluation of the sample remainder 37 is the infiltration rate This is calculated by converting the water permeation data into inches/hour units. This is a simple calculation inasmuch as the volume of water in cup 56 is measured over a set period of time.

The spectrophotometric data relating to the organics content is taken directly from the spectrophotometer, i.e., the output of this unit is given in terms of percent organics for each sample.

The technique of the present invention also provides significant textural analysis and particle size distribution data. In the first step, the total suspended solids are calculated using the 40 second and 2 hour temperature and hydrometer readings. The calculation employing this data is fully described by G. J. Bouyoucous, "Mechanical Analysis by the Hydrometer Method", *Soil Sci.*, Vol. 42, pp. 225–228 (1936), which is incorporated by reference herein. The 2 hour temperature and hydrometer readings are used to calculate the amount of suspended clay in the sample remainder 37, again using the Bouyoucous method. Similarly, the amount of suspended silt is calculated subtracting the total suspended clay value from the total suspended solids value.

The final step involves calculation of the particle size distribution of the sand and gravel content of the sample. The dried classification weights are each multiplied by 2.5 to obtain a percentage value representing the weight of each respective sieve size in the total soil sample.

The foregoing data can then be used by a green's keeper to evaluate important characteristics of the turf. The infiltration rate has found to be particularly important in this evaluation, and experience has proved that the infiltration rate should be from about 6–10 inches per hour, and most preferably about 8 inches per hour.

The total porosity value is also deemed important, along with the relative balance between the capillary and non-capillary porosity. Generally speaking, the total porosity should be from about 35–45%, whereas, ideally, the capillary and non-capillary porosities should be close to equal. Deviations from these preferred porosity values can give the green's keeper important information about turf care. For example, if the non-capillary (air) porosity is low, e.g., 8%, the green's keeper may choose to aerify using a hollow tine-or similar apparatus with refilling of the aeration holes with a straight sand fill.

The bulk density value obtained using the process of the invention should preferably be in the range of 1.4 to 1.5 grams per cubic centimeter. Values below this preferred range (e.g., 1.35 g/cc or less) indicate a turf system developing excess thatch. Values above this range indicate a light turf system.

The percent organics data from the spectrophotometer gives important data concerning turf viability. For example, the percent organics level in each of the segments (i.e., the 0.5–2 inch, 2–3 inch and 3–4 inch segments) of the sample remainder 37 should ideally be within the range of from about 1–2%. Values significantly above or below this range may indicate the need for specific types of soil treatments such as sand/peat application if the organic level is very low, or a sand only application if the organic level is high. However, if the infiltration rate, total porosity, capillary and non-capillary porosities are within an acceptable range, then excess or lower organics value may not present a problem.

EXAMPLE

In this example, a comparative test was run between a conventional turf analysis and the improved process of the present invention. In carrying out these tests, two soil samples were taken side-by-side from a single golf green in Kansas City, Mo.

The individual tests of a conventional turf analysis performed on one of the comparative samples are fully described in the March/April, 1993 issue of USGA Green Section Record, which is incorporated by reference herein. Briefly, this method involves obtaining a core sample by the techniques described herein, and first removing the upper thatch section. This entire remaining core sample is then broken up and mixed to homogeneity, followed by compaction to form a laboratory core. Thereupon, the compacted laboratory core is subjected to water permeability and 40 cm tension table tests as described, along with bulk density, total porosity, capillary porosity, non-capillary porosity and particle size determinations.

This conventional analysis gave the following data:

| Infiltration Rate | 8.61 inches/hr. |
|---|---|
| 40 cm Water Holding | 9.01% |
| Bulk Density | 1.57 g/cc |
| Total Porosity | 35.74% |
| Capillary Porosity | 14.22% |
| Non-Capillary Porosity | 21.52% |
| Organic Level | 1.36% |
| Sand | 96.75% |
| Silt and Clay (Pan) | 3.25% |
| Gravel | 0.00% |
| Sand Particle Sizes | |
| #18 mesh | 2.13% |
| #35 mesh | 13.60% |
| #60 mesh | 54.63% |
| #100 mesh | 20.53% |
| #270 mesh | 5.86% |

This data indicates that the soil sample is essentially within acceptable ranges and should sustain a healthy turf system. However, the green's keeper reported that the turf was actually sparse and difficult to maintain during hot dry weather. Viewing only the conventional data, one would conclude that the turf problem was chemical in nature as opposed to a problem related to the physical characteristics of the seed bed.

The comparative soil sample was tested in accordance with the present invention as fully described above. The data generated from these tests was as follows.

| Infiltration Rate | 0.11 inches/hr. |
|---|---|
| 40 cm Water Holding | 18.41% |
| Bulk Density | 1.51 g/cc |
| % Solids | 57.88% |
| Total Porosity | 42.12% |
| Capillary Porosity | 27.87% |
| Non-Capillary Porosity | 14.25% |
| Feeder Roots | 3.75 inches |
| Root Mass | 0.5 inches |
| Organic Level | |
| 0.5–2 inch layer | 2.27% |
| 2–3 inch layer | 0.69% |
| 3–4 inch layer | 0.46% |
| Sand | |
| 0.5–2 inch layer | 95.68% |
| 2–3 inch layer | 98.22% |
| 3–4 inch layer | 97.14% |
| Silt | |
| 0.5–2 inch layer | 2.17% |
| 2–3 inch layer | 0.89% |
| 3–4 inch layer | 2.06% |
| Clay | |
| 0.5–2 inch layer | 1.90% |
| 2–3 inch layer | 0.89% |
| 3–4 inch layer | 0.80% |
| Gravel | |
| 0.5–2 inch layer | 0.25% |
| 2–3 inch layer | 0.00% |
| 3–4 inch layer | 0.00% |
| Sand Particle Sizes | |
| #18 mesh | |
| 0.5–2 inch layer | 2.88% |
| 2–3 inch layer | 0.58% |
| 3–4 inch layer | 0.58% |
| #35 mesh | |
| 0.5–2 inch layer | 13.63% |
| 2–3 inch layer | 7.40% |
| 3–4 inch layer | 7.73% |
| #60 mesh | |
| 0.5–2 inch layer | 45.75% |
| 2–3 inch layer | 51.28% |
| 3–4 inch layer | 51.80% |
| #80 mesh | |
| 0.5–2 inch layer | 22.28% |
| 2–3 inch layer | 24.50% |
| 3–4 inch layer | 23.40% |
| #100 mesh | |
| 0.5–2 inch layer | 4.53% |
| 2–3 inch layer | 5.73% |
| 3–4 inch layer | 5.25% |
| #140 mesh | |
| 0.5–2 inch layer | 4.18% |
| 2–3 inch layer | 5.93% |
| 3–4 inch layer | 5.45% |

| #270 mesh | |
|---|---|
| 0.5–2 inch layer | 2.43% |
| 2–3 inch layer | 2.80% |
| 3–4 inch layer | 2.93% |

In addition to this data, the time lapse photography taken during the drying of the sample core revealed a dark colored organic layer extending one-half inch below the thatch layer and across the entirety of the core.

The results of the analysis in accordance with the present invention were used to identify the actual problems with the turf in question. In particular, the water permeability results indicated an extremely low permeability, which was the basic problem with the turf. The other data such as the stratified organic content and the porosity data, were not consistent with the extremely low water permeability results. However, the time lapse photographic evidence established that the low water permeability resulted because of an extremely dense layer of organic material, particularly just below the thatch layer in the sample.

In sum, the analysis of the invention established that the green was "sealed off." This refers to a condition typically associated with high water retention and low air porosity and with a very low infiltration rate. The condition can result from factors such as a high content of fines, silt and/or clay, a high content of organic materials such as peat. Experience indicates that the layering of organic material is the more prevalent condition resulting in sealed off seed beds. It has also been found that root mass in a sealed off seed bed rarely penetrates through the dense organic layer. This organic layering was confirmed by the time lapse photography taken in accordance with the present invention. These photographs revealed the existence of a black layer of material directly beneath the thatch layer, which was later identified as organic. Therefore, the analysis of the invention was able to not only confirm a difficulty with the green—wholly undocumented when using the conventional analysis—which was consistent with the green's keeper's experience in the field.

The analysis of the invention also gives the organic content, texture and particle size distribution of respective strata of an undisturbed core sample. Such stratification testing produces substantially different results when compared with the conventional analysis. The organic content of the 0.5–2 inch layer was 2.27% and the content of the next two layers was 0.69% and 0.46% respectively. The conventional analysis gave an undifferentiated organic content of 1.36% for the entire core. The stratified analysis confirmed that the physical problems of the seed bed result from the black organic layer. The test indicated that the black layer is high in silt and clay, which is confirmed by the high capillary porosity and low non-capillary porosity. The black layer did not contain sufficient material for a Bouyoucous test, but a mathematical estimation gives a silt content of 4.74% and a clay content of 3.93%.

This comparative test demonstrates that the assumption of the conventional test—that a homogenized core sample fairly represents the entire seed bed from which the sample was taken—is seriously in error. The conventional system can and does produce significantly incorrect results which would lead to improper conclusions about the condition of the seed bed and appropriate remedial steps. These inherent errors are overcome using the improved method of the invention.

I claim:

1. A soil analysis method comprising the steps of:

obtaining a core sample of soil having an essentially undisturbed, naturally occurring compaction and stratification;

dividing said core sample into a plurality of vertically aligned strata; and separately analyzing each of said strata for at least one of organic content, silt and clay content, and sand content.

2. The method of claim 1, including the step of determining the particle size distribution of said sand content in each of said strata.

3. The method of claim 1, including the step of analyzing each of said strata for organic content.

4. The method of claim 1, including the step of analyzing each of said strata for silt and clay content.

5. The method of claim 1, including the step of analyzing each of said strata for sand content.

6. The method of claim 1, including the step of recording data generated from said analyzing step.

* * * * *